United States Patent
Oi et al.

(10) Patent No.: US 6,928,770 B2
(45) Date of Patent: *Aug. 16, 2005

(54) ALTERNATING LAYER NON-EDIBLE FORAGING MATRIX CONFIGURATIONS FOR CRAWLING ARTHROPODS

(75) Inventors: Faith M. Oi, Gainesville, FL (US); Philip G. Koehler, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/613,405

(22) Filed: Jul. 3, 2003

(65) Prior Publication Data

US 2004/0068919 A1 Apr. 15, 2004

Related U.S. Application Data

(60) Division of application No. 09/942,341, filed on Aug. 29, 2001, now Pat. No. 6,637,150, which is a continuation-in-part of application No. 09/525,086, filed on Mar. 14, 2000.
(60) Provisional application No. 60/159,266, filed on Oct. 13, 1999, and provisional application No. 60/243,905, filed on Oct. 27, 2000.

(51) Int. Cl.[7] .............................................. A01M 1/20
(52) U.S. Cl. ........................ 43/131; 43/132.1; 43/107; 43/124; 43/121; 106/15.05; 424/411; 424/84
(58) Field of Search ................................ 43/131, 132.1, 43/107, 124, 121; 106/15.05; 424/411, 84

(56) References Cited

U.S. PATENT DOCUMENTS

| 2,931,140 A | 4/1960 | Laffler et al. ................. 47/48.5 |
| 3,700,687 A | * 10/1972 | Hoffmann et al. .......... 548/111 |
| 3,835,578 A | 9/1974 | Basile ........................... 43/132 |
| 3,940,875 A | 3/1976 | Basile ........................... 43/124 |

(Continued)

FOREIGN PATENT DOCUMENTS

| GB | 2306886 | 5/1997 | |
| JP | 56151759 A | * 11/1981 | ........... C08L/95/00 |
| WO | WO 01/26456 A1 | 4/2001 | ............ A01M/1/20 |

OTHER PUBLICATIONS

*Laboratory Evaluation I of Insecticides for Control of Tarnished Plant Bug in Mississippi,* research report from University of Mississippi website, 1995, (pp. 1 and 2 of 3).
*Letter to Kandy Walker Duke at Rhone Merieux from New York State Department of Environmental Conservation* letter dated Feb. 7, 1997, obtained from website address: pmep.cce.cornell.edu, updated Dec. 16, 1997, (pp. 1 x2 of 3).
*Rhône–Poulenc's Fipronil give approval for Clorox Products,* press release from library section of website www.rhone–poulenc.com, Aug. 5, 1997, last updated Feb. 11, 1998, 1 page.

(Continued)

*Primary Examiner*—Peter M. Poon
*Assistant Examiner*—Andrea M. Valenti
(74) *Attorney, Agent, or Firm*—Brian S. Steinberger; Law Offices of Brian S. Steinberger, P.A.

(57) ABSTRACT

Below ground kits, methods, apparatus and configurations for controlling arthropods such as termites, ants, and roaches. An embodiment has alternating layers of a first layer consisting of a mixture of a non-edible foraging matrix mixed with a slow-acting and non-repellant toxicant, where the first layer is adjacent to another layer of non-toxic edible/attractant materials allow for the treatment of different arthropods. The non-edible foraging matrix can be selected from at least one of: soil, gravel, rocks, pebbles, shale, and mixtures thereof. The nontoxic layer can include materials such as foam and cellulose. Different arthropods such as termites, fire ants, carpenter ants, and roaches can be treated with the subject embodiments.

12 Claims, 12 Drawing Sheets

U.S. PATENT DOCUMENTS

| | | | | |
|---|---|---|---|---|
| 3,972,993 | A | * 8/1976 | Kobayashi et al. | 424/416 |
| 4,043,073 | A | 8/1977 | Basile | 43/124 |
| 4,970,822 | A | 11/1990 | Sherman | 43/131 |
| 5,057,315 | A | 10/1991 | Gunner et al. | 424/93 |
| 5,057,316 | A | 10/1991 | Gunner et al. | 424/93 |
| 5,100,107 | A | * 3/1992 | Latta | 256/19 |
| 5,435,096 | A | 7/1995 | Nekomoto | 43/112 |
| 5,555,672 | A | * 9/1996 | Thorne et al. | 43/124 |
| 5,592,774 | A | 1/1997 | Galyon | 43/124 |
| 5,778,596 | A | 7/1998 | Henderson et al. | 43/132.1 |
| 5,815,090 | A | 9/1998 | Su | 340/870 |
| 5,935,943 | A | 8/1999 | Asai et al. | 514/63 |
| 5,950,356 | A | 9/1999 | Nimocks | 43/131 |
| 5,979,108 | A | * 11/1999 | Adams | 43/121 |
| 6,052,066 | A | 4/2000 | Su | 340/870.16 |
| 6,058,646 | A | 5/2000 | Bishoff et al. | 43/131 |
| 6,079,150 | A | 6/2000 | Setikas et al. | 43/132.1 |
| 6,219,961 | B1 | * 4/2001 | Ballard et al. | 43/131 |
| 6,298,597 | B1 | * 10/2001 | Koehler et al. | 43/131 |
| 6,370,812 | B1 | 4/2002 | Burns et al. | 43/124 |
| 6,397,516 | B1 | 6/2002 | Su | 43/124 |
| 6,606,816 | B2 | * 8/2003 | Oi et al. | 43/131 |
| 6,606,817 | B2 | * 8/2003 | Oi et al. | 43/131 |
| 6,637,150 | B1 | * 10/2003 | Oi et al. | 43/131 |
| 2002/0134003 | A1 | * 9/2002 | Oi et al. | 43/131 |
| 2002/0157302 | A1 | * 10/2002 | Oi et al. | 43/131 |

OTHER PUBLICATIONS

*Toxicity and Degradation of Fipronil Applied to Cotton for Control of Boll Weevils,* Joseph E. Mulrooney and Deepa Goli, interpretive summary for TEKTRAN website address www.nal.usda.gov, Dec. 3, 1997, p. 1 of 2.

*Fipronil,* NPTN fact sheet on Fipronil from National Pesticide Telecommunications Network website, 5 pages, Dec. 1997.

*Prospective Study Comparing Fipronil with dichlorvos/fenitrothion and methoprene/pyrethrins in contol of Flea Bite Hypersensitivity in Cats,* R.G. Harvey, E.J. Penaliggon, and P. Gautier, Veterinary Record (1997), www.inno–vet.com, page 1.

Website www.peteducation.com, general information on Fipronil as used in flea prevention and treatment 1997, 3 pages.

*Control of Corn Root Warm in Green Peas,* WSU cooperative extension research report, Washington State University, www.agsyst.wsu.edu, last updated Jul. 24, 2000, pp. 1 to 5.

*Residue Analysis of Fipronil and its Metabolites Observec in Leek Samples,* Guido Goller, Patrick Duchene and Marc Maestracci, report available on website www.chemsoc.org, no date listed, one page.

*Evaluation of Fipronil for residual control of mole crickets on turfgrass,* Table of results using Fipronil to treat mole crickets on turfgrass, no date listed, one page.

*Field Trials to Evaluate the Efficacy of Fipronil (regent R) for Controlling Rice Insects Under Different Formulations,* Luuong Minh Chau, report posted on website www.chemsoc.org, no date listed, two pages.

*Maxforce Bait Gel–FC–German Roaches,*www.roachcontrol.com. website advertisement for Maxforce Gel FC, no date listed.

* cited by examiner

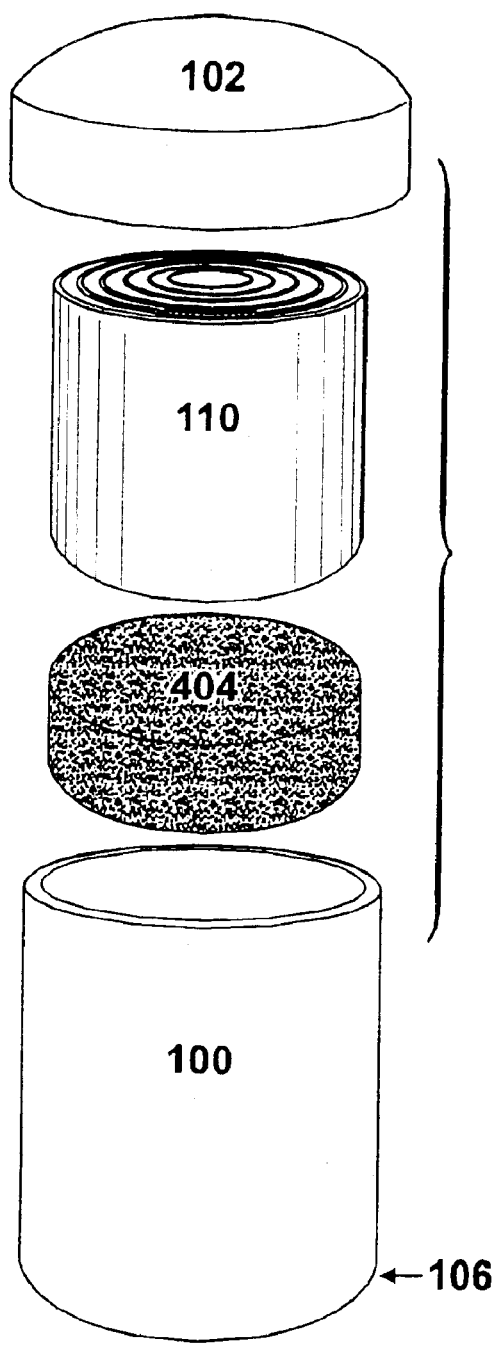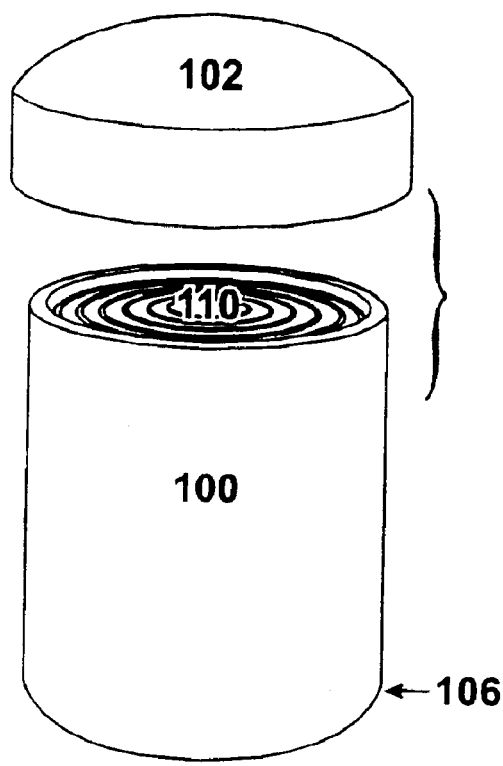
FIG. 2A
FIG. 2B

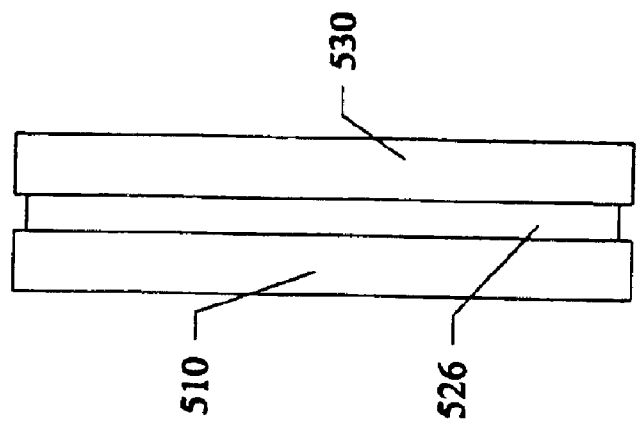
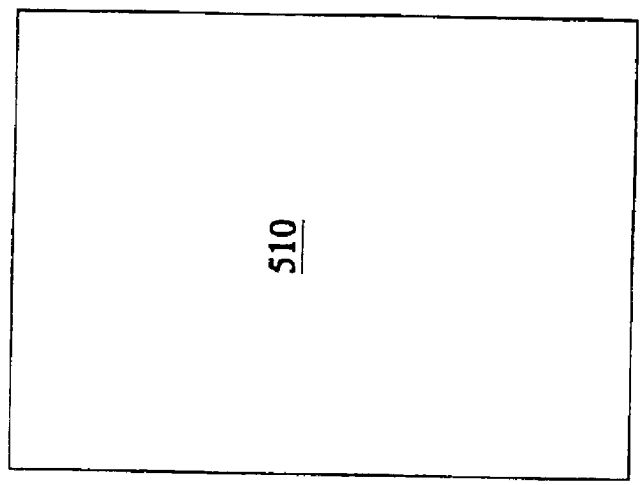
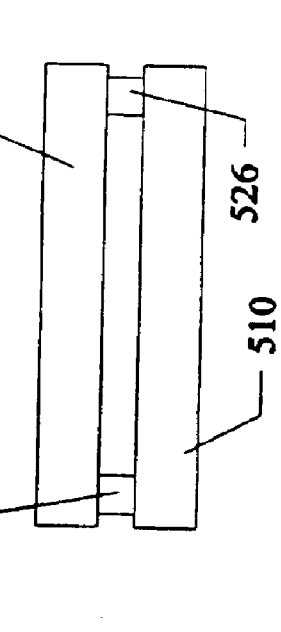
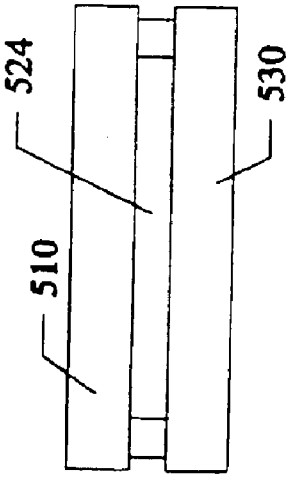

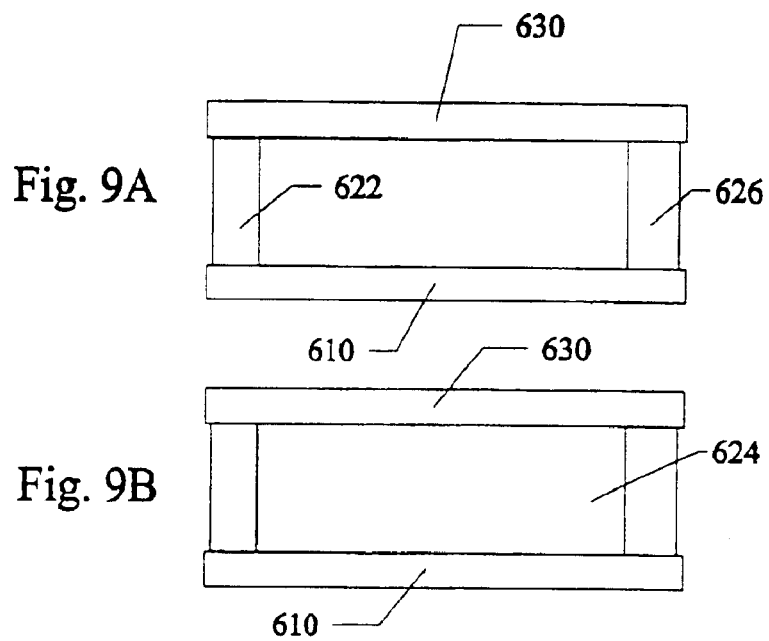
Fig. 9A
Fig. 9B
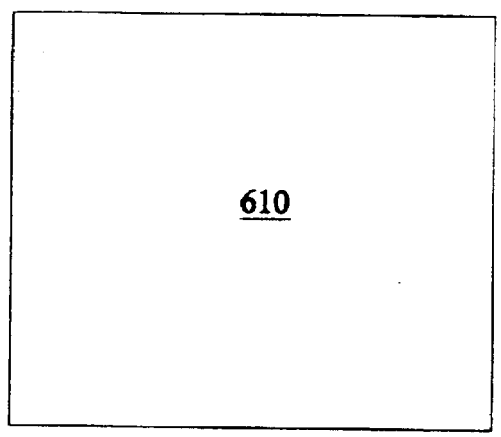
Fig. 9C
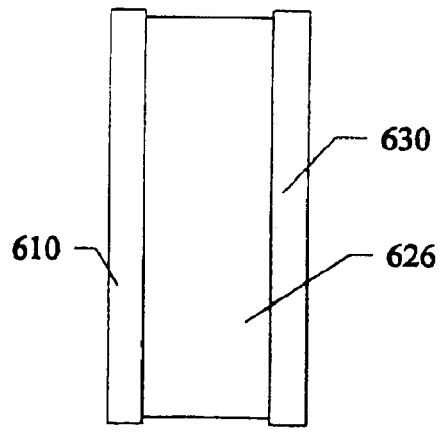
Fig. 9D

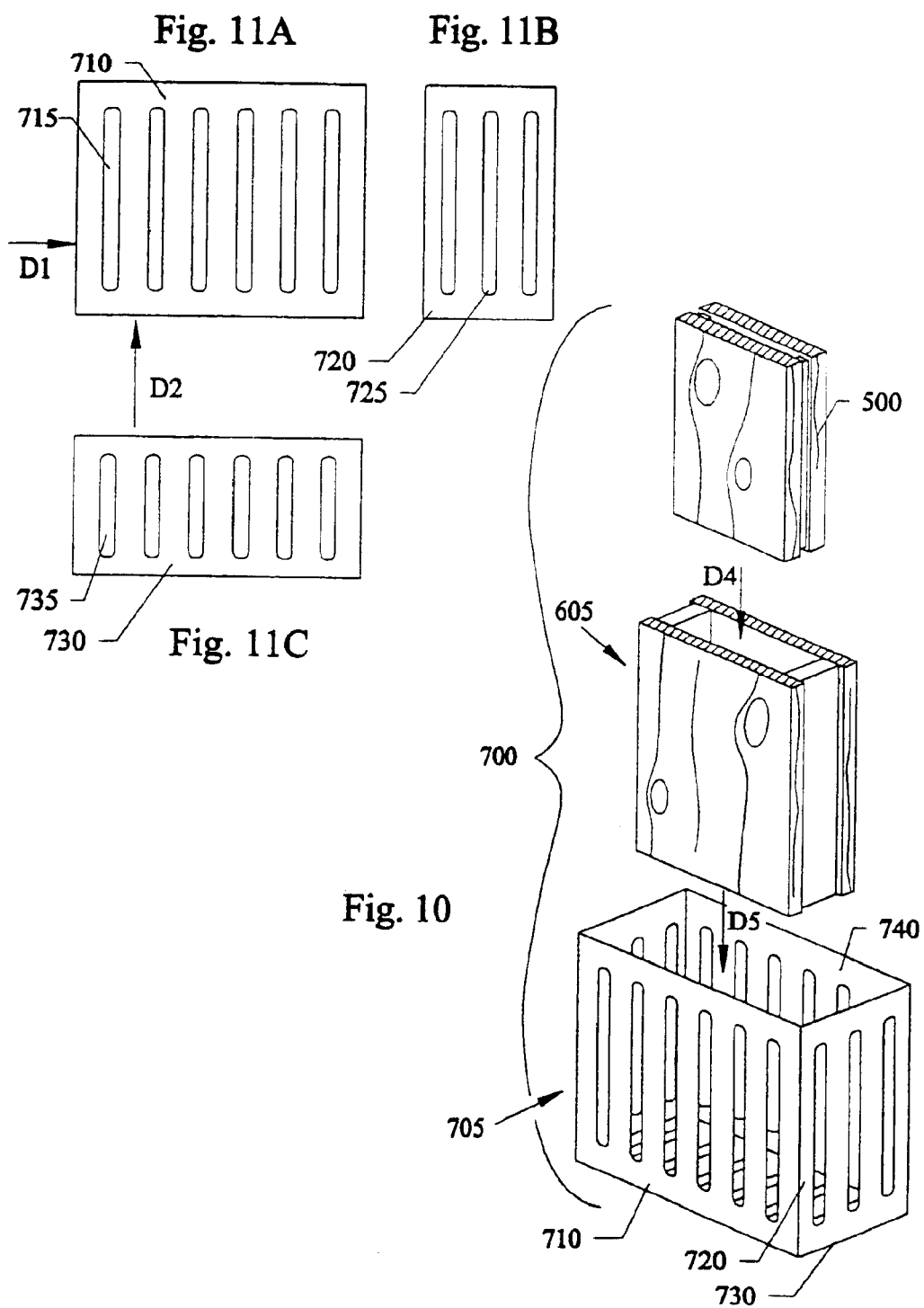

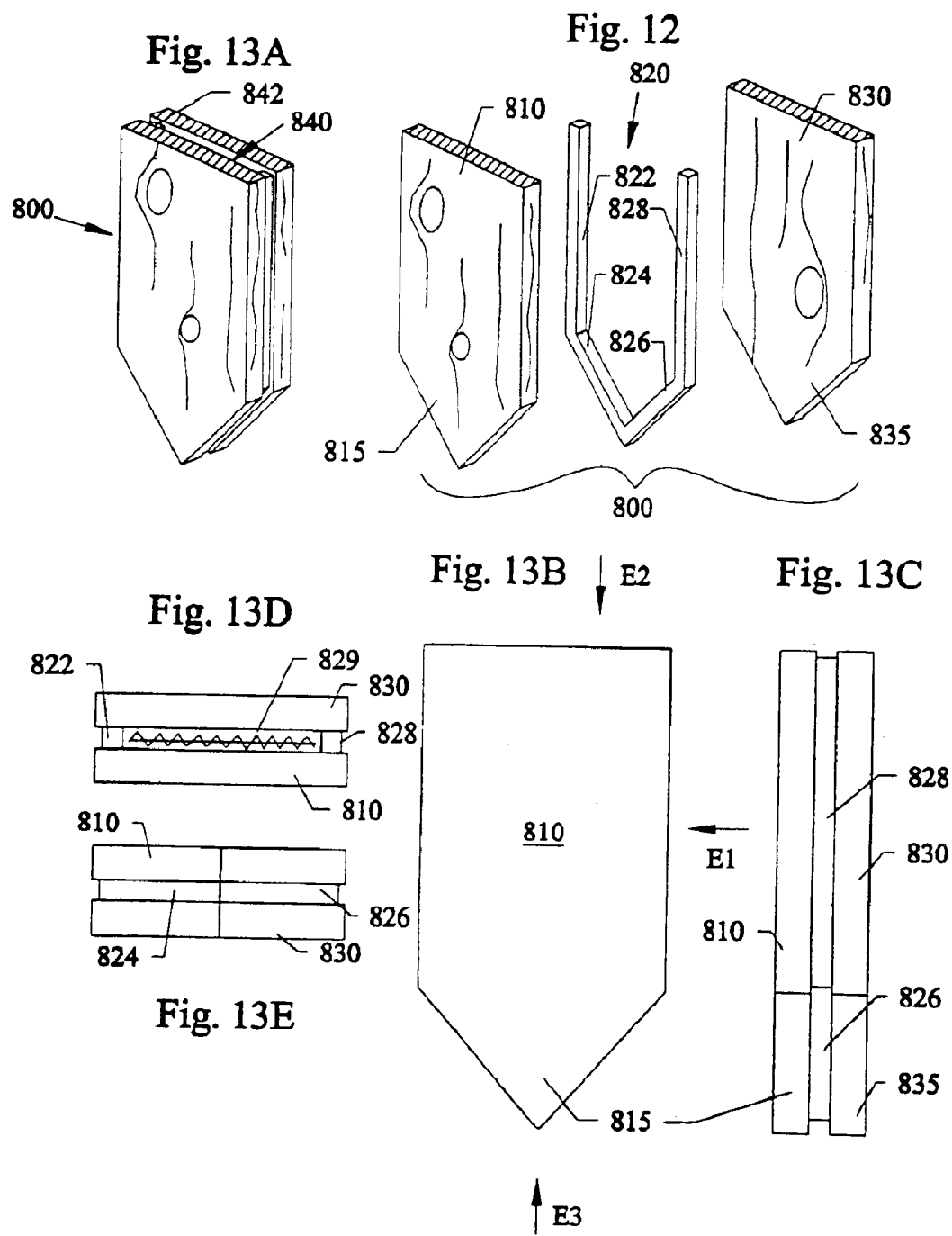

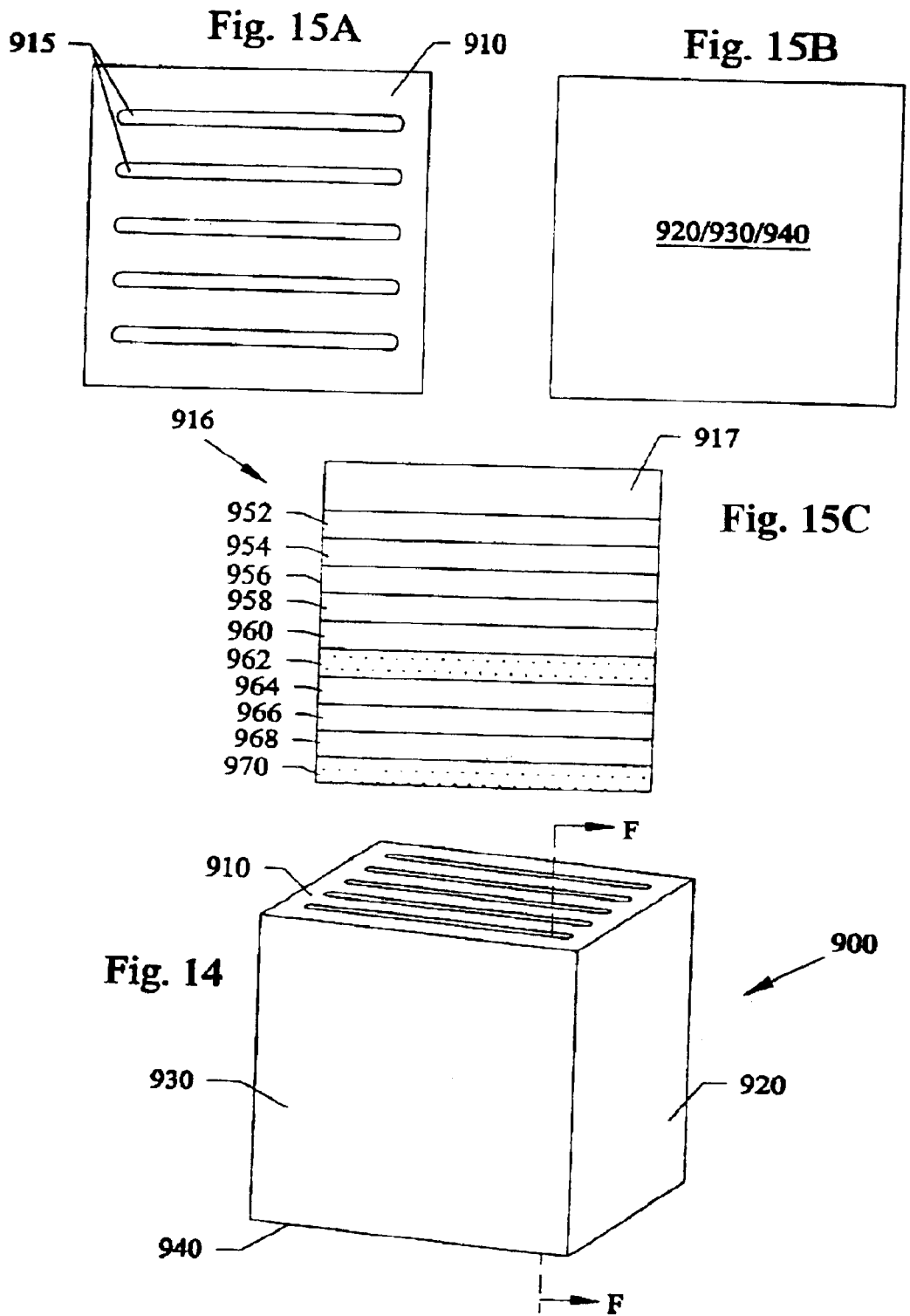

ALTERNATING LAYER NON-EDIBLE FORAGING MATRIX CONFIGURATIONS FOR CRAWLING ARTHROPODS

This invention claims the benefit of priority to U.S. provisional application No. 60/243,905 filed Oct. 27, 2000, by the same inventors and assignee as the subject invention, and this invention is a division of application Ser. No. 09/942,341, filed Aug. 29, 2001, now U.S. Pat. No. 6,637,150, which is Continuation-In-Part of U.S. Pat. No. 09/525,086 filed Mar. 14, 2000 by the same inventors and a co-assignee as the subject application, now allowed, and which claims the benefit of priority to U.S. provisional application No. 60/159,266 filed on Oct. 13, 1999.

This invention relates to arthropod control for arthropods such as termites, carpenter ants, fire ants and roaches, and in particular to an apparatus and method for below ground applications using a non-toxic food source to attract the arthropods into a housing having a non-edible foraging matrix treated with a slow acting and non-repellant toxicant, that causes the arthropods to take the toxicant back to the galleries and living areas of their colony.

BACKGROUND AND PRIOR ART

Arthropods such as termites, carpenter ants, fire ants and roaches have been a common nuisance pest. In southern regions especially Florida, termites are considered to be one of the most destructive arthropod pests for structures. The two forms of subterranean termites that are of concern for pest control are subterranean termites, which typically nest in the ground and usually maintain some sort of ground connection, and drywood termites, which start as a pair in a piece of wood and do not have a ground connection. Subterranean termites are the most damaging termites and usually enter buildings from the surrounding soil.

Over the years there have been at least several methods of subterranean termite control. For example, the most common method of subterranean termite control requires soil underlying a structure to be treated with a termiticide barrier (usually hundreds of gallons of termiticide per house) to prevent termites from entering the structure from the ground. From 1950 to 1988 chlorinated hydrocarbons were the main method of barrier treatment to control subterranean termites. However, environmental concerns with those chemical treatments resulted in the loss of chlorinated hydrocarbons that lasted up to 35 years in the soil. Chemicals that replaced the chlorinated hydrocarbons for barrier treatment have had a high rate of failure resulting in extensive termite damage to structures.

Problems with the barrier treatments become further compounded since builders have often been known to dump substantial amounts of edible building materials, such as wood and cardboard into the underlying soil that can serve as guidelines into the structures and provide a substantial food source, increasing the probability of termite infestation in the structure.

Over the years, different techniques and systems have also been proposed to enhance the underground delivery of toxic insecticides beneath structures. See for example, U.S. Pat. Nos. 3,940,875 and 4,043,073 to Basile; and U.S. Pat. No. 4,625,474 to Peacock. However, many of these techniques and systems such as Basile '073 are concerned with trying to refresh the initial termiticide barrier by having the termites chew through a container with the toxicant (for example. Other examples of these techniques and systems allow for installing a piping system during the building construction process so that additional termiticide can be pumped under a slab of the building at intervals after construction. Furthermore, some of these techniques and systems such as the Basile '073 patent utilized a toxicant (for example, dieldrin) that has been banned by the EPA (Environmental Protection Agency) for termite treatment. Additionally, the pipe delivery systems have been known to often got clogged after installation making the pipe delivery systems not usable.

Still other well-known subterranean termite treatment techniques and systems include bait techniques, which require termites to forage into a monitor that contains a non-toxic food source. Once termites infest the non-toxic food source, a food source laced with a toxicant (toxic bait) is replaced into the monitor. Termites continue to recruit to the monitor and feed on the toxic bait. Consumption and trophallaxis (feeding other termites) of the toxic bait later causes many termites to die. See for example, U.S. Pat. Nos. 5,329,726 to Thorne et al.; U.S. Pat. No. 5,899,018 to Gordon et al.; and U.S. Pat. No. 5,950,356 to Nimocks. However, these techniques generally require that the termites consume the toxic bait. Termites refuse to consume most toxicants; therefore this technique is useful for only 2–3 toxicants currently known in the world. Termites also refuse to consume bait food sources that are contaminated with molds or are too wet. These bait techniques do not use a non-edible foraging matrix (described in the subject invention), such as soil and sand, to cause the termites to tunnel therethrough and carry the non-edible particles treated with toxicant to the galleries and living spaces of the colony; thus contaminating them. Most toxicants applied to non-edible foraging matrix, except the repellent pyrethroids, will be picked up and carried by termites to other areas of their tunnel system.

Other systems have been proposed but still fail to overcome the problems with the methods and applications described for the cited patents above. U.S. Pat. No. 3,972,993 to Kobayashi et al. requires a membrane treated with a substance attractive to termites (due to the termite's innate searching and feeding behavior, termites are not attracted to food from a distance when allowed to forage without interference) so that when the termites chew through the membrane a toxic surface is contacted. U.S. Pat. No. 5,501,033 to Wefler delivers a liquid toxic food source for social insects like yellowjackets and has very little use for termites. U.S. Pat. No. 5,609,879 to Myles requires the laborious harvesting of termites from the ground, sponging on an insecticidal epoxy, and returning them to the soil. U.S. Pat. No. 5,778,596 to Henderson et al. is a device for delivering toxic food for termites to consume. And U.S. Pat. No. 5,921,018 to Hirose provides foraging guidelines for termites to follow so they enter a device that captures and kills them.

There are additional problems with prior art treatments that use repellent liquids, non-repellent liquids, and baits. When using repellent liquids, the liquid barriers need to be applied in a perfectly continuous fashion. If gaps in the treatment exist, especially with repellent termiticides, such as those belonging to the pyrethroid class, the termites will forage and find the gaps in the treatment, increasing the probability of infesting the structure.

In non-repellent liquid treatments, the termites are not able to detect that they are in a treated area; hence the classification "non-repellent," and they die. A major drawback for non-repellant liquid treatments is that liquid termiticides in this class are still so new that there are questions about how long they will last in the soil, especially when exposed to sun and weather. The present invention protects the foraging matrix from sun and weather to prolong its usability, and the foraging matrix can be continuously replaced as necessary to recharge the system. The application of liquid termiticide barriers requires several hundred gallons of insecticide that are pumped under houses, some-times resulting in contamination of the house interior and water supply wells. Most homeowners want applications that are less intrusive and disruptive.

Bait type station techniques and systems are again not practical since the bait stations require a food source that is palatable to termites. Selecting the appropriate food source can be difficult. While wood is a known food source, wood is very inconsistent in composition, so manufacturers don't like to use it for use with toxicants. Other known food sources such as paper food sources have other problems. For example, if paper is not packed tightly enough, it will be emptied by termites and not deliver enough toxicant to kill large numbers of termites. Most cellulose material will rot when placed in the soil. Once the food goes bad, termites will not feed, rendering the bait ineffective.

The subject invention uses a non-edible foraging matrix treated with a slow-acting non-repellent toxicant. Termites put the particles of the treated matrix into their mouths when they tunnel through it, and many toxicants will work because they do not need to consume it and feed it to others. The particles are returned to the colony and incorporated into their tunnels. Termites that contact the particles die several days after the toxicant on the matrix particles are contacted. The behavior of the termites moves the treated foraging matrix from the exit and entrance opening of the device's chamber to contaminate their colony and tunnels.

SUMMARY OF THE INVENTION

The first objective of the present invention is to provide a method and system for killing arthropods such as termites, carpenter ants, fire ants and roaches over time and protecting structures.

The second objective of this invention is to provide a method and system for destroying arthropods such as termites, carpenter ants, fire ants and roaches using a non-toxic and edible food source to attract the arthropods and only causing the arthropods to tunnel through non-edible particles treated with a slow-acting and non-repellant toxicant when the arthropods return to their colonies so that the arthropods contaminate their galleries and living spaces with the particles.

The third objective of this invention is to use soil particles, sand particles, mixtures or other non-edible foraging matrices as a method of dispersing the toxicant to—arthropods such as termites, carpenter ants, fire ants and roaches that pass through tunnels, galleries, and living spaces.

The fourth objective of this invention is to use various housings that can be inserted into the ground for treating arthropods such as termites, carpenter ants, fire ants and roaches.

Preferred embodiments of the method and apparatus of killing arthropods such as termites, carpenter ants, fire ants and roaches and protecting structures. The method includes the steps of: inserting a nontoxic food source such as wood, paper, cardboard, and cellulose-based material, into a chamber, positioning the chamber adjacent to arthropods and allowing the arthropods to enter and eat the nontoxic food source, inserting a foraging non-edible matrix treated with a slow acting and non-repellent toxicant into the chamber so that the foraging matrix is between the non-toxic food sources, and allowing the arthropods to exit from the chamber, wherein the slow acting and non-repellent toxicant destroys the arthropods in their colonies over time and protects structures.

The chamber can be sandwich shaped, cylindrical shaped, disc shaped and the like. The chamber can include a removable cap so the chamber can be serviced through time, and/or include narrow tip stake bottoms for allowing easy insertion when being pushed into the ground.

The chambers can be substantially composed of materials that will naturally decompose over time such as wood and cellulose, and the like. Alternatively, the outer walls of the chambers can include an outer frame formed from a long lasting material such as rust resistant metal, aluminum, plastics, and the like, having openings therethrough, so that interior chambers containing the mixtures of the non-edible foraging matrix and slow-acting toxins can be changed, substituted, replenished over time.

The non-edible foraging matrix can be chosen from soil, sand, gravel, rocks, pebbles, shale, combinations thereof, and the like. The non-edible foraging matrix can be poured into the chamber or be separated inserted into another chamber that can be put into the first chamber.

Toxicants suitable for use are slow acting, non-repellant toxicants for control of arthropods such as termites, carpenter ants, fire ants and roaches. For termite applications, these toxicants can include but are not limited to for example chlorinated nicotine derivatives such as fipronil and imidachoprid; organophosphates such as chlorpyrifos; pyrroles such as chlorfenapyr. A preferred embodiment of the slow acting and non-repellent toxicant can include approximately 1.25 ppm to approximately 12.5 ppm of fipronil. The slow acting and non-repellent toxicant can also include approximately 2.5 ppm to approximately 25 ppm of chlorfenapyr. The slow acting and non-repellent toxicant can also include approximately 0.5 ppm to approximately 50 ppm of imidacloprid. The slow acting and non-repellent toxicant can also include approximately 0.5 to approximately 50 ppm of chlorpyrifos or other toxicants that is not repellent to the termites.

Still further applications can include multiple layers of mixtures of non-edible foraging matrix and slow-acting toxins, and edible type materials such as cellulose and Styrofoam that allows different types of arthropods such as termites and, fire ants and carpenter ants to be treated with the same device.

Further objects and advantages of this invention will be apparent from the following detailed description of a presently preferred embodiment, which is illustrated schematically in the accompanying drawings.

BRIEF DESCRIPTION OF THE FIGURES

FIGS. 2A and 2B are exploded views of a single monitor with a chamber containing a non-toxic food source and a treated non-edible foraging matrix disc that is placed between the non-toxic food and the termite exit from the chamber.

FIG. 7B is a top view of the embodiment of FIG. 7A along arrow B1.

FIG. 7C is a bottom view of the embodiment of FIG. 7A along arrow B2.

FIG. 7D is a front view of the embodiment of FIG. 7A along arrow B3.

FIG. 7E is a side view of the embodiment of FIG. 7A along arrow B4.

FIG. 9A is a top view of the main outer housing of FIG. 8 along arrow C1.

FIG. 9B is a bottom view of the embodiment of FIG. 8 along arrow C2.

FIG. 9C is a front view of the embodiment of FIG. 8 along arrow C3.

FIG. 9D is a side view of the embodiment of FIG. 8 along arrow C4.

FIG. 10 is an exploded view of a fourth embodiment of the invention.

FIG. 11A is a front/back view of a frame holder for the fourth embodiment.

FIG. 11B is a side view of the frame holder of FIG. 11A along arrow D1.

FIG. 11C is a bottom view of the frame holder of FIG. 11A along arrow D2.

FIG. 12 is an exploded view of a fifth embodiment of the invention.

FIG. 13A is an assembled view of the fifth embodiment of FIG. 12.

FIG. 13B is a front view of the fifth embodiment of FIG. 12.

FIG. 13C is a side view of the embodiment of FIG. 13B along arrow E1.

FIG. 13D is a top view of the embodiment of FIG. 13B along arrow E2.

FIG. 13E is a bottom view of the embodiment of FIG. 13B along arrow E3.

FIG. 14 is a perspective view of a sixth embodiment of the invention.

FIG. 15A is a top view of the sixth embodiment of FIG. 14.

FIG. 15B is a side view or bottom view of the sixth embodiment of FIG. 14.

FIG. 15C is a cross-sectional view of the sixth embodiment of FIG. 14 along arrow F.

DESCRIPTION OF THE PREFERRED EMBODIMENTS

Figure 1:
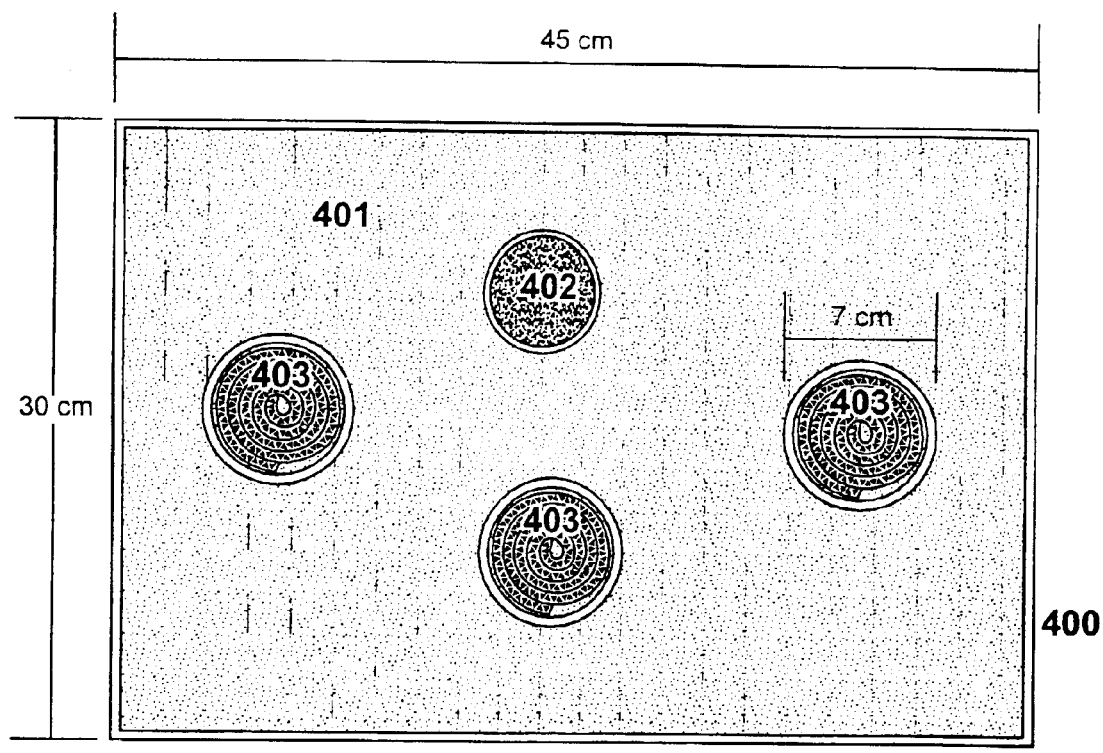
FIG. 1 shows an experimental setup for testing the novel treatment apparatus and method.

Before explaining the disclosed embodiment of the present invention in detail, it is to be understood that the invention is not limited in its application to the details of the particular arrangement shown since the invention is capable of other embodiments. Also, the terminology used herein is for the purpose of description and not of limitation.
First Embodiment The subject invention was tested recently at the USDA-ARS Center for Medical, Agricultural, and Veterinary Entomology, at Gainesville, Fla.

Data from two sets of experiments are included. In the first set of experiments, a total of 3,000 termites were used (2,970 workers and 30 soldiers) in all three replicates. In the second set of experiments, 3,000 termites were used in 4 replicates and 1,400 termites (1,386 workers and 14 soldiers) were used in two replicates for a total of six replicates. Fewer termites from 2 colonies were used because we could not collect enough to complete the replicates if a total of 3000 termites were used. The termites (*Reticulitermes flavipes* (Kollar)) were field collected from field colonies, separated from debris, and held in the laboratory at the USDA (United States Department of Agriculture) for no more than 14 days before introduction into a test arena for each experimental block. Termites from a different colony were used for each replicate.

The test arena consisted of Plexiglas sides (45 cm long, by 30 cm wide by 5.5 cm high) taped to a glass bottom (45 cm long, by 30 cm wide, by 0.6 cm high) with clear packing tape, manufactured by Crystal Clear, Manco Inc., Avon, Ohio. The Plexiglas sides were assembled by joining pieces with methylene chloride. Before the Plexiglas sides were taped to the glass bottom, the sides were baked in an oven at 40+/−2° C. for 24 hours to ensure that any volatiles caused by the methylene chloride were removed.

Builders sand from Unified Classification SP, O'Steen Bros., Inc., of Gainesville, Fla., was oven dried at 60+/−2° C. for at least 24 hours in metal pans. The sand was cooled and sieved using a sieve manufactured from Fisher Scientific Co., USA sieve no. 25, having openings of approximately 0.0278 inches each. The sieve was used to remove large pieces of debris. Two thousand five hundred grams (+/−1 g) of sand were poured into the arena and mixed thoroughly with 250 ml of double filtered, de-ionized water, which brought the moisture content of the sand to 10%. The sand was tamped and leveled.

Three monitoring stations were placed on top of the moistened builder's sand. The monitors were made of one roll of corrugated cardboard (100 cm by 6.5 cm) that was moistened and stacked into a white PVC coupler having an inner diameter of approximately 7 cm and being approximately 7.3 cm high, manufactured from Lasco of Brownsville, Tenn.

The non-edible foraging matrix treated with toxicant and used for the testing was a loamy, siliceous, thermic, arenic paleudults soil, which was a common sandy loam native soil from Central Florida. This native soil was initially oven dried at 150+/−2° C. for at least 24 hours, then cooled, then sifted to remove large pieces of organic debris. After treatment with a toxicant, the treated non-edible foraging matrix was formed into a disc for insertion into the monitors after termite activity occurred. The color contrast between the builder's sand, which was light honey color, and the native non-edible foraging matrix, which was a dark brown, was enough to see termites move portions of the treated soil particles from the discs into the tunnels.

In both sets of experiments, three different non-edible foraging matrix treatment applications were prepared using novel selected amounts of termite treatment chemicals. The difference between the first experiment and the second experiment was the rates used. In the first experiment, the first application had a non-edible foraging matrix sample treated with 50 ppm of imidacloprid, a version entitled Premise from the Bayer Corp. of Kansas City, Kans. The second application had the non-edible foraging matrix sample treated with 250 ppm of chlorfenapyr, a version entitled Phantom from American Cyanamid of Princeton, N.J. A third application had the non-edible foraging matrix treated with 125 ppm of fipronil, a version entitled Termidor, from Rhone-Poulenc of Research Triangle, N.C.

In the second experiment, the first application had a non-edible foraging matrix sample treated with 0.5 and 5.0 ppm of imidacloprid, a version entitled Premise from the Bayer Corp. of Kansas City, Kans. The second application had the non-edible foraging matrix sample treated with 2.5 and 25.0 ppm of chlofenapyr, a version entitled Phantom from American Cyanamid of Princeton, N.J. A third application had the non-edible foraging matrix treated with 1.25 and 12.5 ppm of fipronil, a version entitled Termidor, from Rhone-Poulenc of Research Triangle, N.C. It is important to note that the rates used were approximately 10 and 100 times less than the rates use in the first experiment and are also 10 to 100 times less than the rates listed or proposed on the pesticide labels. Thus, the rates used in this experiment was not used for the intended purpose of the chemicals, which was to immediately kill the termites by creating a chemical barrier completely around the structure.

In both experimental set ups, controls were treated with filtered and de-ionized water. The treated non-edible foraging matrix was air dried for 7 days and stored in sealed plastic bags until ready for use.

Discs of treated non-edible foraging matrix were prepared by thoroughly moistening 100 grams (+/−5 g) of treated non-edible foraging matrix with about 10 ml of filtered, de-ionized water. Monitors were lined with a double layer of paper towels (28 cm by 22.5 cm) manufactured by Somerset paper towels of Bernardsville, N.J. The non-edible foraging matrix was packed into the paper towel lined PVC coupler, which produced the non-edible foraging matrix disc having dimensions of approximately 7 cm diameter by approximately 2 cm high. The excess paper towel was twisted and sealed with a rubber band so that the treated non-edible foraging matrix would not contaminate the surrounding area until the termites had tunneled through it.

After allowing the termites to forage for 7 days in the arenas, the termites were sampled from each of the infested monitors by removing the cardboard roll, separating out the termites, and counting the live ones. The treated non-edible foraging matrix disc was introduced into the base of the monitor that contained the most termites. The treated non-edible foraging matrix disc was placed in the bottom of the monitor and a new, moistened cardboard roll (100 cm by 4 cm) was placed on top. The PVC coupling unit was placed so that the non-edible foraging matrix disc was in contact with the builder's sand. Termites were returned to their respective monitors that were provisioned with new cardboard rolls by gently pouring them into the tops of the monitors. The number of termites recovered from each of the three monitors was recorded weekly for eight weeks. The total number of termites recovered from all three monitors was calculated, and the mean and standard error for each treatment and the control was calculated and reported weekly for 8 weeks.

Both experiments were designed as a randomized complete block, blocking on colony for each termiticide. In the first experiment, treatments included a control and 3 termiticides at one concentration, replicated 3 times for a total of 12 experimental units. In the second experiment treatments included a control and 3 termiticides at two concentrations, replicated six times for a total of 48 experimental units. Treatment effects on percent termite survival were analyzed by analysis of variance (ANOVA) and Tukey's HSD (SAS Institute 1996) which, when used in combination, indicate which treatments were significantly different from each other in killing termites under our conditions.

In the first experiment, numbers of termites in untreated arenas were consistently higher than numbers of termites in arenas with a treated disc of foraging matrix inserted at the base of one of the 3 monitors. Both 125 ppm fipronil and 250 ppm chlorfenapyr killed all termites in the arenas by 7 weeks after setup, and 50 ppm imidacloprid had only 54 termites in the monitors (See Table 1). We noticed that the treated non-edible foraging matrix had been moved from the discs into the galleries, contaminating the termite tunnels and living areas. Termites from the sand in the foraging tray were not recovered or counted.

TABLE 1

Numbers of termites in monitors within experimental arenas treated with foraging matrices containing 50 ppm imidacloprid, 125 pm fipronil, and 250 ppm chlorfenapyr. Untreated discs were foraging matrices were treated with water.

| | Mean ± SE number of termites in monitors for | | | |
|---|---|---|---|---|
| Week | Fipronil | Chlorfenapyr | Imidacloprid | Untreated |
| 1 | 73.8 ± 11.1 | 100 ± 11.9 | 82.0 ± 2.7 | 80.4 ± 5.0 |
| 2 | 44.3 ± 18.8 | 60.7 ± 12.9 | 67.5 ± 0.1 | 68.0 ± 8.7 |
| 3 | 14.6 ± 8.0 | 21.3 ± 12.2 | 45.7 ± 14.9 | 66.1 ± 8.0 |
| 4 | 6.4 ± 3.4 | 10.9 ± 7.6 | 13.7 ± 2.9 | 47.8 ± 8.2 |
| 5 | 2.6 ± 1.6 | 3.5 ± 3.3 | 8.0 ± 3.7 | 30.9 ± 8.8 |
| 6 | 0.3 ± 0.3 | 0.8 ± 0.8 | 3.2 ± 3.0 | 23.8 ± 9.1 |
| 7 | 0 ± 0 | 0 ± 0 | 1.4 ± 1.4 | 17.2 ± 7.5 |
| 8 | 0 ± 0 | 0 ± 0 | 1.8 ± 0.9 | 11.6 ± 8.4 |

In the second experiment, termite survival in arenas was counted when termite activity in the monitors was not detected. Time for cessation of termite activity was 5 weeks for fipronil and 8 weeks for chlorfenapyr and imidacloprid (Table 2). For chlorfenapyr, percent survival was 0.16% for the 25 ppm foraging matrix and 9.33% for the 2.5 ppm foraging matrix compared with 20.92% survival in the untreated arenas. Therefore the chlorfenapyr killed virtually all the termites at 25 ppm. For fipronil, percent survival was 0.3–0.5% for 12.5 and 1.25 ppm foraging matrix compared with 39% in the untreated arenas. Therefore, fipronil killed virtually all the termites at 1.25 and 12.5 ppm. For imidacloprid, percent survival was 17% for 0.5 and 5.0 ppm foraging matrix compared with 23% in the untreated arenas; indicating that the experiment could have been run longer for imidacloprid or that a higher dose of toxicant could have been used. In all cases the treated foraging matrix was moved from the discs and incorporated into the termite tunnels and living space killing termites as they contacted the treated non-edible foraging matrix particles.

TABLE 2

Mean survival of termites in experiment arenas with foraging matrix discs treated chlorfenapyr or imidacloprid after 8 weeks and with fipronil after 5 weeks. Untreated discs were treated with water.

| Treatment | Mean ± SE percent survival of termites |
|---|---|
| Chlorfenapyr 2.5 ppm | 9.33 ± 5.05a[1] |
| Chlorfenapyr 25.0 ppm | 0.16 ± 0.16b |
| Untreated | 20.92 ± 6.89a |
| Fipronil 1.25 ppm | 0.51 ± 0.30b |
| Fipronil 12.5 ppm | 0.30 ± 0.29b |
| Untreated | 39.28 ± 8.11a |
| Imidacloprid 0.5 ppm | 17.13 ± 11.61a |
| Imidacloprid 5.0 ppm | 17.57 ± 9.36a |
| Untreated | 23.44 ± 10.89a |

[1]Means followed by the same letter are not significantly different.

FIG. 1 shows the experimental set up for testing the novel treatment apparatus and method. The bottom of the arena 400 is covered with builders sand 401. Termites are released into the arena in a release chamber 402. There are 3 monitors 403 (PVC tubes containing cardboard) to monitor numbers of termites. After termites are established one of the monitors is selected to receive a treated foraging matrix disc at the termite entrance and exit of the monitoring tube.

FIG. 2 is an exploded view of a monitor (PVC tube 100 with a removable cap 102 and a rolled cardboard food source 110) with a treated non-edible foraging matrix disc 404. The capped tube 100 has an open end 106 that serves as an entrance and exit for the termites.

Figure 3:
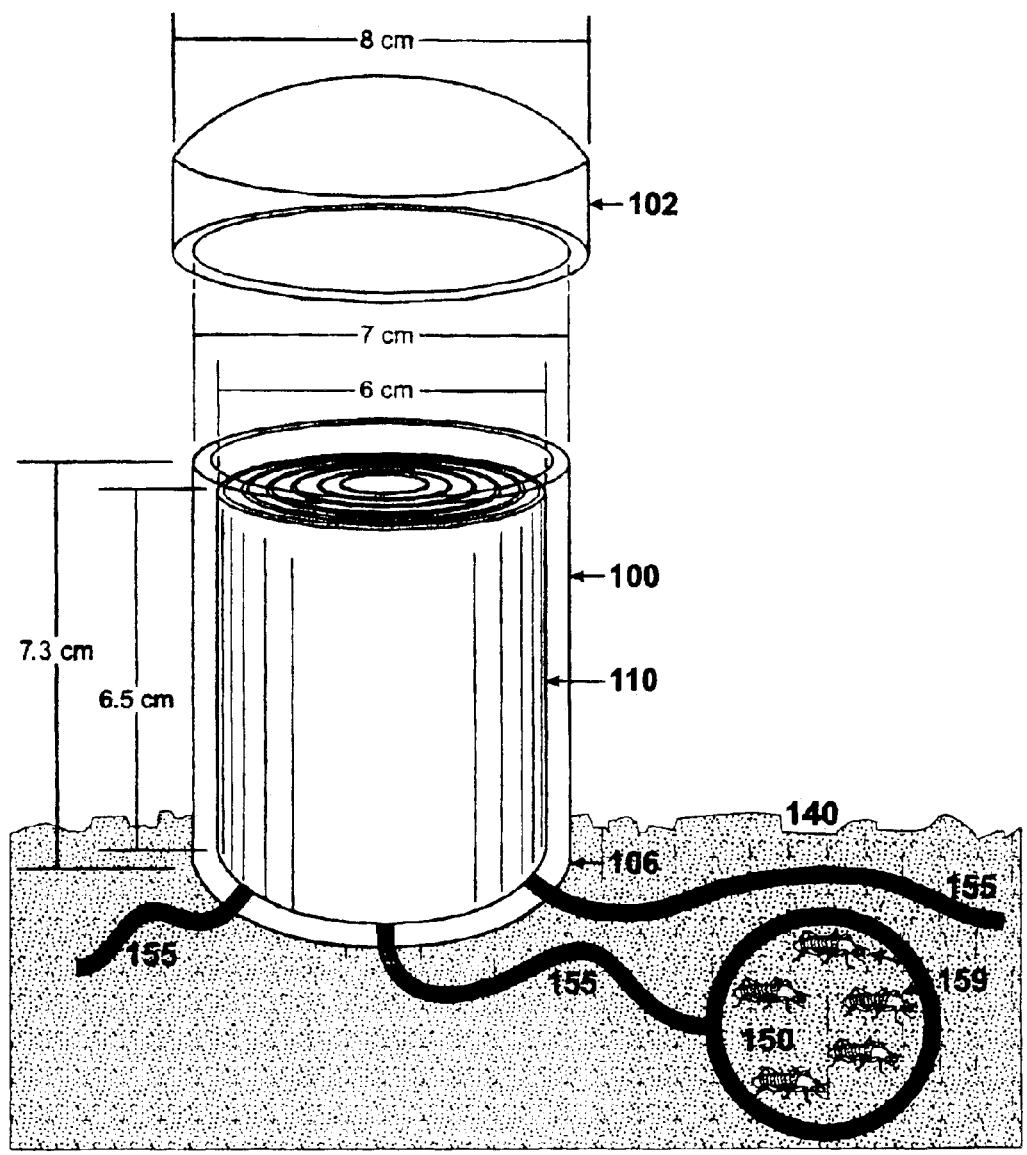
FIG. 3 shows an the first step of using a chamber with edible non-toxic food source used to attract termites.

FIG. 3 shows the first step of using a monitor with an edible nontoxic food source used to attract termites. Referring to FIG. 3, a PVC tube 100 has a removable cap 102, and an open end 106. An edible non-toxic food source 110 (cardboard) is inserted into the open end 106 of the tube 100. The open end 106 of tube 100 is then inserted into the ground adjacent to tunnels 155 leading to a termite colony 150 so that termites 159 can be directed to pass through the open end 106 of the tube to eat the food source 110.

Figure 4:
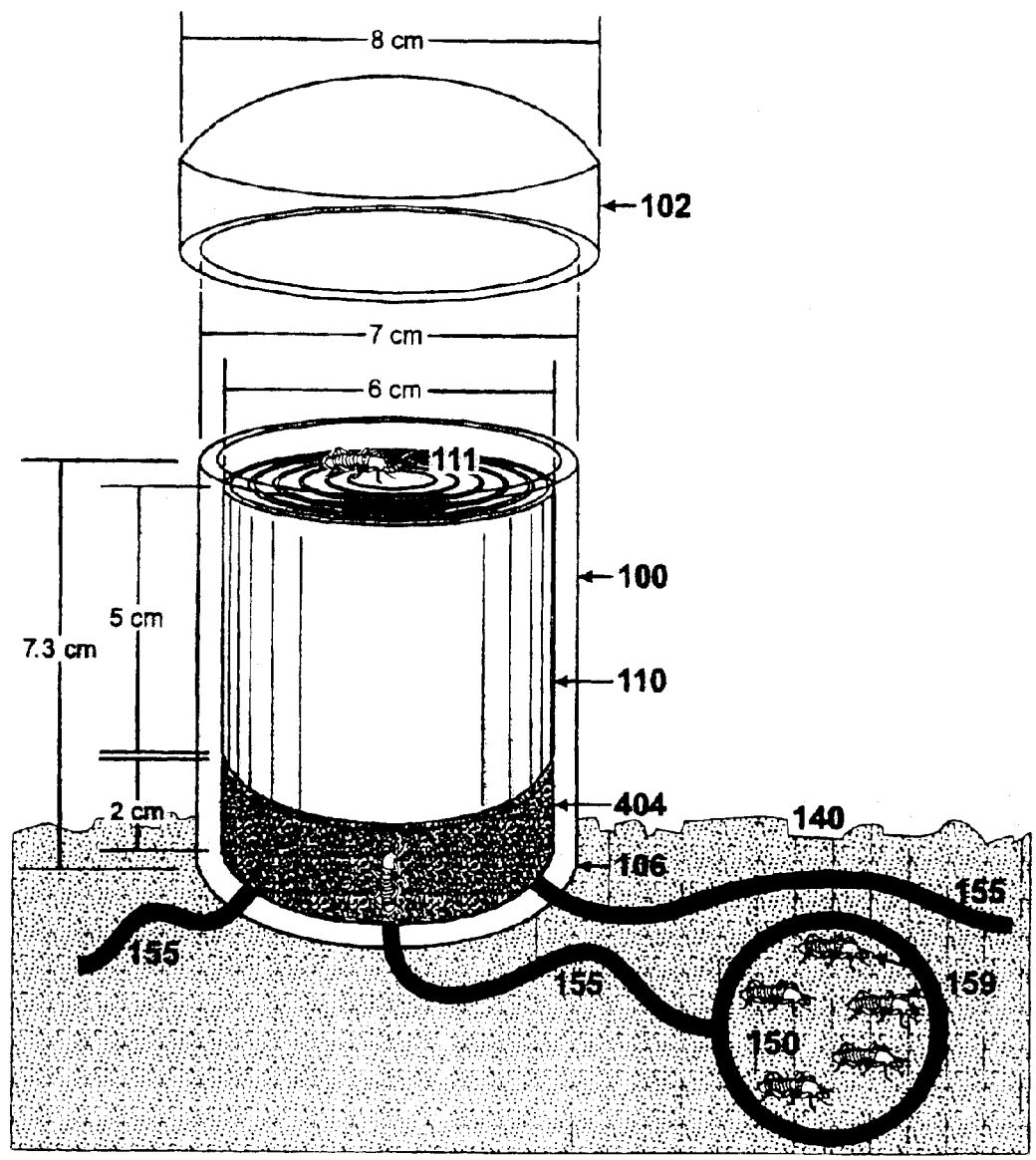
FIG. 4 shows a second step of inserting a non-edible foraging matrix treated with a slow-acting and non-repellant toxicant between the food source having active termite infestation inside the chamber and the only exit for the chamber.

FIG. 4 shows a second step of inserting a non-edible foraging matrix treated with a slow acting and non-repellant toxicant between a food source having active termite infestation inside the chamber and the only exit for the chamber. Referring to FIG. 4, a non-edible foraging matrix, such as a disk of non-edible foraging matrix 404, treated with a slow acting and non-repellant toxicant is inserted into the opening 106 of tube 100 between the food source 110 having infested termites 111 therein and the ground 140 with a termite tunnel 155 connecting the termite colony 150 in the soil to the food source 110.

Figure 5:
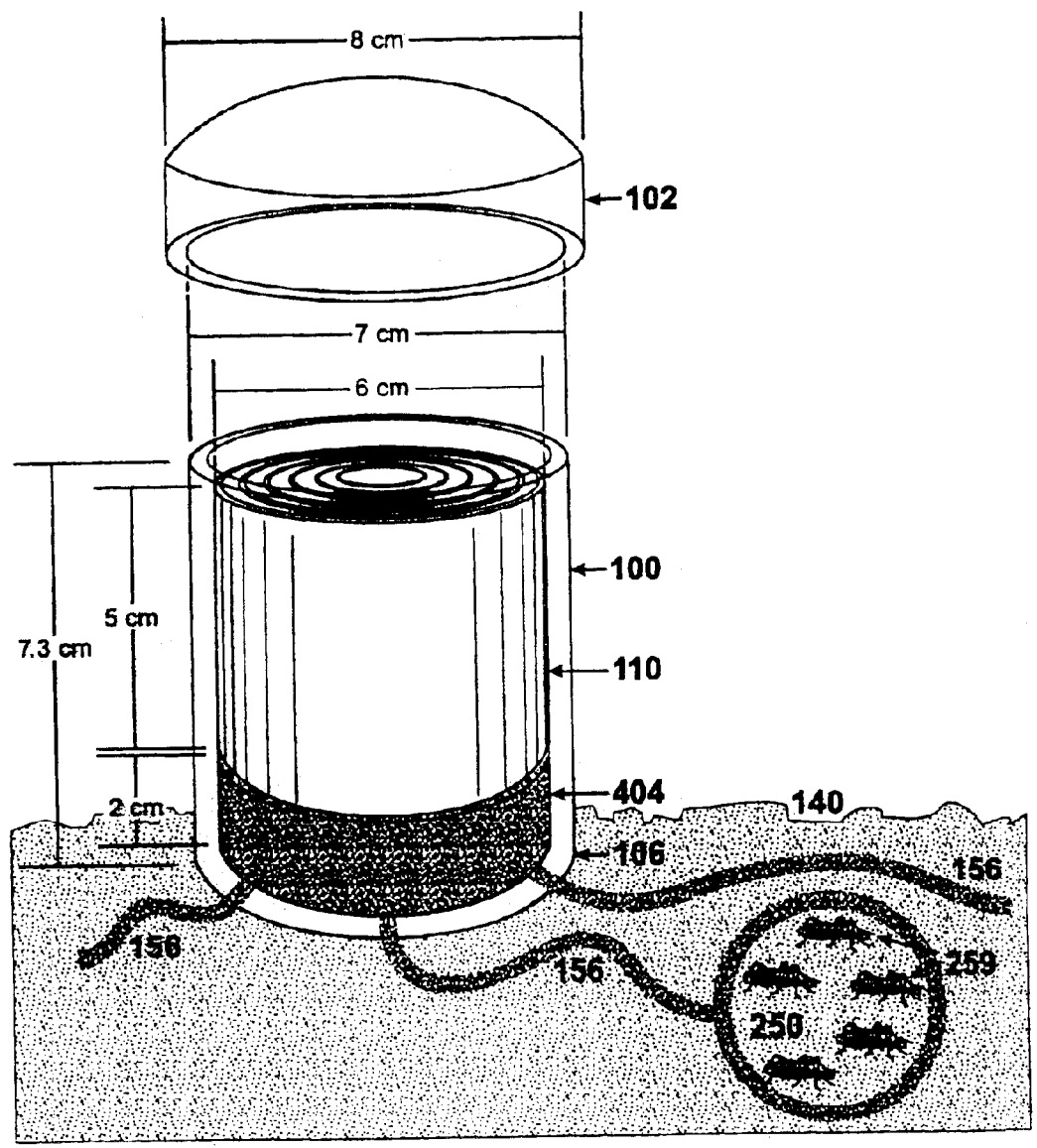
FIG. 5 shows a third step of the termites having passed through the foraging matrix and now contaminating their tunnels and colonies with the slow acting non-repellant toxicant.

FIG. 5 shows a third step of the termites having tunneled through the non-edible foraging matrix disk 404 and now moving the treated non-edible foraging matrix and creating contaminated tunnels 156 and contaminated colonies 250 with the slow acting non-repellant toxicant. Termites returning from the food source 110 are forced to tunnel through the non-edible foraging matrix disk. The termites remove contaminated particles of the non-edible foraging matrix as they pass back into the soil. The contaminated termites 259 incorporate the treated non-edible foraging matrix particles into their tunnels 156 and contaminate the rest of the colony 250. The slow acting toxicant in the non-edible foraging matrix particles kills and destroys termites 259 over time after they contact it in their tunnels 156 and in their colonies 250.

The nonedible foraging matrix can be wrapped in various materials such as but not limited to thin plastic film (i.e. Saran Wrap®), and the like.

While the preferred embodiment refers to a PVC tube chamber, the chamber can be of various configurations such as but not limited to cylindrical, square, rectangular, and the like.

Although the preferred embodiment is described for use as a device placed in the ground to kill subterranean termites, a similar device could be placed on wood in structures to kill subterranean termites tunneling into houses and feeding on wood within houses.

The invention can be used to protect all type of cellulose containing structures such as but not limited to manmade structures such as buildings, walls, and the like and natural structures such as trees, and the like.

Second Embodiment

Figure 6:
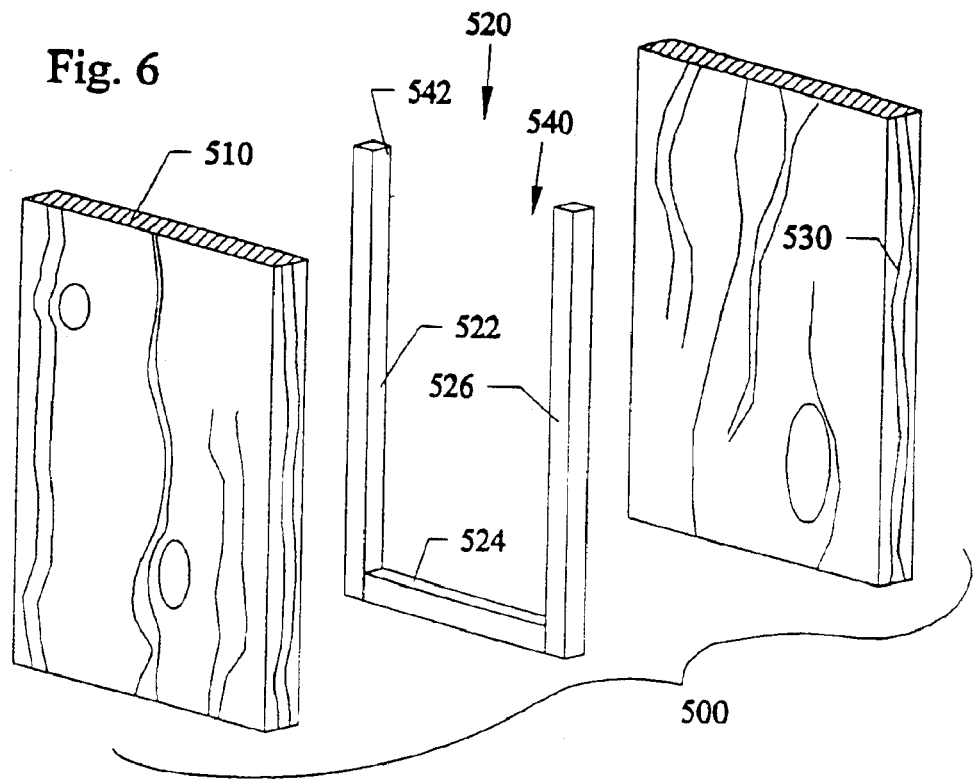
FIG. 6 is an exploded view of a second embodiment box application of the subject invention.
Figure 7A:
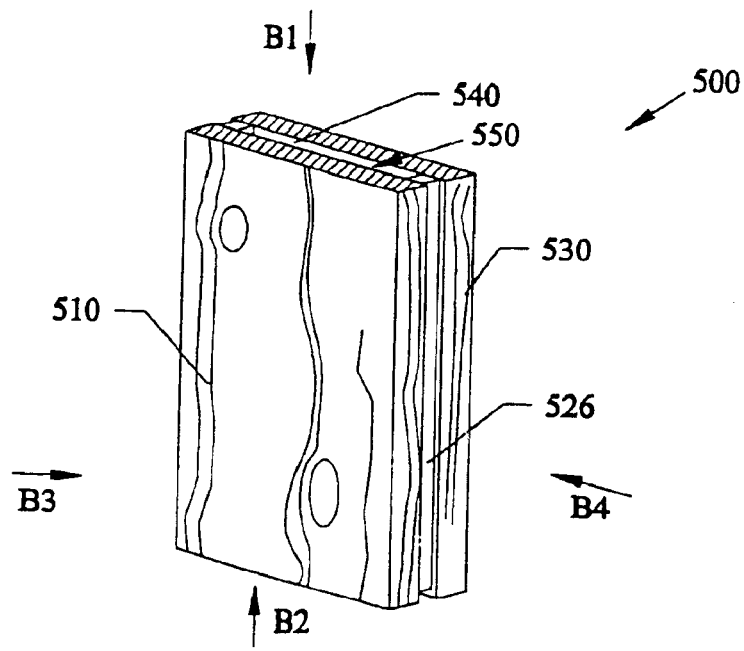
FIG. 7A is a perspective view of the second embodiment of FIG. 6.

FIG. 6 is an exploded view of a second embodiment box application 500 of the subject invention. FIG. 7A is a perspective view of the second embodiment 500 of FIG. 6. FIG. 7B is a top view of the embodiment 500 of FIG. 7A along arrow B1. FIG. 7C is a bottom view of the embodiment 500 of FIG. 7A along arrow B2. FIG. 7D is a front view of the embodiment 500 of FIG. 7A along arrow B3. FIG. 7E is a side view of the embodiment 500 of FIG. 7A along arrow B4.

Referring to FIGS. 6 and 7A–7E, embodiment 500 can have a rectangular outer shape, having a first wall 510 and second wall 530 that can be sandwiched together with side perimeter members 522, 524, 526 all together forming a chamber space 540 therebetween. Walls 510, 530 and side perimeter members 522, 524, 526 can each be formed from an edible non-toxic food source such as wood, paper, cellulose material, foam, plastic, combinations thereof, and the like, that can be fastened together by for example, with a non-toxic adhesive such glue, and the like. For example, a preferred embodiment 500 can have walls 510, 530 formed from wood, side perimeter members 522, 524, 526 formed from foam, and glue joining these components together in a sandwich configured chamber 500. The upper portion 542 of inner space 540 can be open to allow the mixture 550 of the slow acting toxicant and non-edible foraging matrix to be inserted inside.

Approximate dimensions of the second embodiment 500 can includes a thickness of approximately 13 mm and a longitudinal length of approximately 51 mm, and a short width length of approximately 37 mm. The upper portion opening 542 can also include a cap member similar to the other members 522, 524, 526 can be used to close off the mixture of the slow acting toxicant mixed with the non-edible foraging matrix from being physically touched by the user. Still furthermore, a see-through material member such as clear plastic can be used to also cap the upper portion opening 542.

In application, the second embodiment 500 can be used in applications similar to those of the first embodiment that was previously described. For example, embodiment 500 can be inserted into the ground adjacent to termites. The insertion can be done by placing the embodiment 500 into an existing hole in the ground. Still furthermore, the embodiment 500 can be manually pushed into the ground in selected locations about a structure that is to be protected. Similar to the first embodiment, arthropods such as termites here would be attracted to the edible food source walls 510, 530, and/or side perimeter members 522, 524, 526 and would then pass into the interior space 540 having the mixture 550 of the non-edible foraging matrix and slow acting toxicants that were previously described in the first embodiment, and then they would pass out of the chamber embodiment 500 to bring the slow acting toxicants back to their tunnels, colonies, nests, and the like, where the slow acting toxicants would kill the termites over time. Similar to the first embodiment the mixture 550 of slow acting toxicants and non-edible foraging matrix can be pre-packaged in a covering. Still furthermore, the mixture 550 can be poured into the opening 542 and into the chamber space 540 when it is about to be used.

In the first experiment for embodiment two, oven dried Alachua fine soil was treated with approximately 125.0 ppm chlorfenapyr as the non-edible foraging matrix 550. The mixture 550 was poured into the opening 542 and wet to a moisture level of 10%. The amount of mixture 550 added to opening 542 was recorded for each replicate. Circular plastic containers having a diameter of approximately 11.5 cm by approximately 10 cm thick were filled with approximately 514 g of builder's sand and wet to a moisture level of approximately 10%. Embodiment 2 was inserted into the builder's sand in the plastic cup, 500 subterranean termites were added and the termites were allowed to tunnel for 3 weeks. After 3 weeks, the plastic container setup was disassembled. The number of live termites in the experimental unit was recorded. The amount of mixture 550 displaced from embodiment 2 was measured and recorded. These data are summarized in Table 3. Data were analyzed with a comparison test, between an untreated control sample and four replications(experimental units) of chlorfenatyr (slow acting toxicant).

TABLE 3

Summary of mortality and amount of soil moved when treated with approximately 125.0 ppm chlorfenapyr.

| Treatment | Replications | Alive | % Mortality | Soil Moved (g) |
|---|---|---|---|---|
| Untreated Control | 1 | 456 | 8.8 | 3.93 |
| Chlorfenapyr 125 | 1 | 0 | 100.0 | 1.45 |
| Chlorfenapyr 125 | 2 | 0 | 100.0 | 2.30 |
| Chlorfenapyr 125 | 3 | 1 | 99.8 | 1.28 |
| Chlorfenapyr 125 | 4 | 0 | 100.0 | 0.92 |

Alive refers to number of termites alive after three(3) weeks exposure. %Mortality refers to percentage of termites that died after three(3) weeks exposure. Soil Moved(g) refers to total amount soil removed by the termites per each replication(per experimental unit). Mortality was significantly higher in experimental units with mixture 550 treated with approximately 125.0 ppm chlorfenapyr when compared with the untreated replications(units). An average of 99.95% of the termites in treated units died, compared with 8.8% mortality in the control unit. Additionally, significantly more of the untreated mixture 550 was moved into the termite galleries and living spaces when compared with the treated mixture. Total untreated mixture 550 moved from embodiment 2 to the surrounding area was approximately 3.93 g, compared with an average of approximately 1.49 g of mixture 550 treated with approximately 125.0 ppm chlorfenapyr.

In the second experiment, mixture 550 was tested at a concentration of approximately 12.5 ppm chlorfenapyr. Experimental procedure was identical to what is listed above. Results of the comparison are summarized in Table 4.

TABLE 4

Summary of mortality and amount of soil moved when treated with approximately 12.5 ppm chlorfenapyr.

| Treatment | Replications | Alive | % Mortality | Soil Moved (g) |
|---|---|---|---|---|
| Untreated Control | 1 | 398 | 20.4 | 3.57 |
| Untreated Control | 2 | 441 | 11.8 | 2.85 |
| Untreated Control | 3 | 439 | 12.2 | 3.62 |
| Untreated Control | 4 | 447 | 10.6 | 4.02 |
| Untreated Control | 5 | 444 | 11.2 | 3.51 |
| Chlorfenapyr 12.5 | 1 | 4 | 99.2 | 2.22 |
| Chlorfenapyr 12.5 | 2 | 0 | 100.0 | 2.84 |
| Chlorfenapyr 12.5 | 3 | 361 | 27.8 | 2.64 |
| Chlorfenapyr 12.5 | 4 | 3 | 99.4 | 3.37 |
| Chlorfenapyr 12.5 | 5 | 0 | 100.0 | 3.47 |

Mortality was significantly higher in experimental units with mixture 550 treated with approximately 12.5 ppm chlorfenapyr when compared with untreated replications. An average of approximately 85.3% of the termites in treated units died, compared with approximately 13.2% mortality in the untreated control units. Additionally, there was no significant difference between the amount of treated and untreated mixture 550 moved into the termite galleries and living spaces. Average untreated mixture 550 moved from embodiment 2 to the surrounding area was approximately 3.51 g, compared with an average of approximately 2.91 g of mixture 550 treated with approximately 12.5 ppm chlorfenapyr.

In conclusion, the mortality and amount of treated mixture 550 moved in experimental units containing approximately 125 ppm and approximately 12.5 ppm chlorfenapyr were substantially identical. There were no significant differences in mortality. However, significantly more mixture 550 treated at 12.5 ppm was moved into termite galleries and living spaces when compared with mixture 550 treated at 125.0 ppm chlorfenapyr.

In summary, because there is no significant difference in mortality between mixture 550 treated with approximately 125.0 ppm and approximately 12.5 ppm chlorfenapyr, and significantly more treated mixture 550 is moved into the termite galleries and living spaces with approximately 12.5 ppm chlorfenapyr, we conclude that approximately 12.5 ppm chlorfenapyr is the preferred concentration for embodiment two.

Third Embodiment

Figure 8:
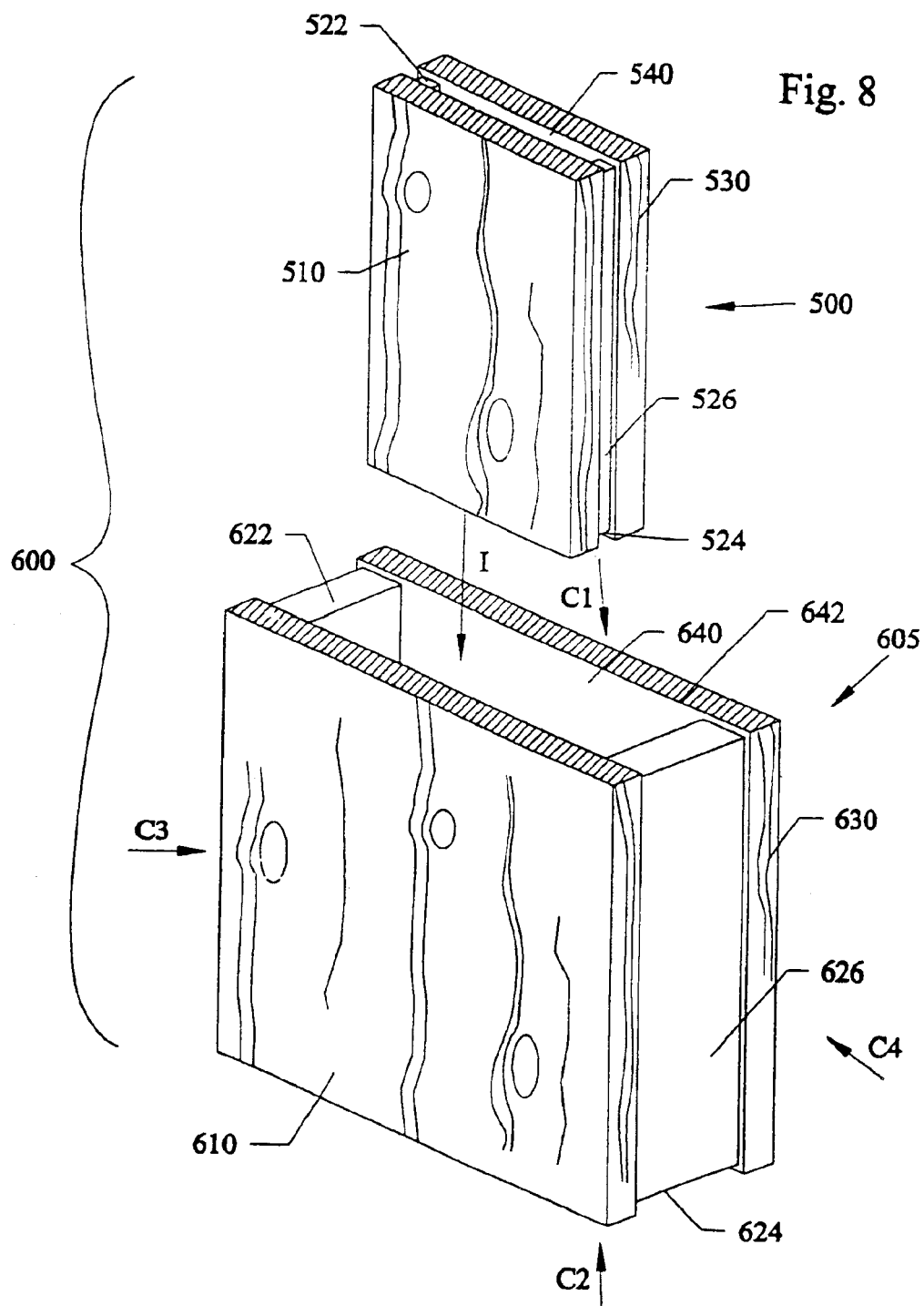
FIG. 8 is an exploded view of a third embodiment of the invention.

FIG. 8 is an exploded view of a third embodiment 600 of the invention. FIG. 9A is a top view of the main outer housing 605 of FIG. 8 along arrow C1. FIG. 9B is a bottom view of the embodiment 600 of FIG. 8 along arrow C2. FIG. 9C is a front view of the embodiment 600 of FIG. 8 along arrow C3. FIG. 9D is a side view of the embodiment 600 of FIG. 8 along arrow C4.

Referring to FIGS. 8 and 9A–9D, embodiment 600 includes a main housing 605 having a front wall 610, back wall 630 and side perimeter members 622, 624, 626 sandwiched there between and that forms a chamber 640 inside accessible by an upper opening 642. Walls 610, 630 and side perimeter members 622, 624, 626 can each be formed from an edible non-toxic food source such as wood, paper, cellulose material, foam, plastic, combinations thereof, and the like, that can be fastened together by for example, with a non-toxic adhesive such glue, and the like. For example, main housing chamber 605 can have walls 610, 630 formed from wood, side perimeter members 622, 624, and 626 formed from foam, and glue joining these components together in a sandwich configuration 605. The upper portion 642 of inner space 640 can be open to allow the insertion of housing 500 to be inserted inside in the direction of arrow I.

Similar to the second embodiment, embodiment 600 can be inserted into the ground adjacent to termites. The insertion can be done by placing the embodiment 600 into an existing hole in the ground. Still furthermore, the embodiment 600 can be manually pushed into the ground in selected locations about a structure that is to be protected. Similar to the previous embodiments, arthropods such as termites here would be attracted to the edible food source walls 610, 630, and/or side perimeter members 622, 624, 626 and would then pass into the interior space 640 having the second housing 500 therein which houses the mixture 550 of the non-edible foraging matrix and slow acting toxicants that were previously described. The termites would bring the slow acting toxicants back to their tunnels, colonies, nests, and the like, where the slow acting toxicants would kill the termites over time.

Approximate dimensions of the third embodiment 600 can includes a thickness of approximately 28 mm and a height length of approximately 60 mm, and a width length of approximately 70 mm.

In the first experiment for embodiment 3, oven dried Alachua fine soil was treated with approximately 125.0 ppm chlorfenapyr as the non-edible foraging matrix 550. The mixture 550 was poured into the opening 542 and wet to a moisture level of 10%. The amount of mixture 550 added to opening 542 was recorded for each replicate. Plastic containers (approximately 11.5 cm diameter, approximately 10 cm high) were filled with approximately 514 g of builder's sand and wet to a moisture level of approximately 10%. Embodiment 3 was assembled and inserted into the builder's sand in the plastic cup, 500 subterranean termites were added and the termites were allowed to tunnel for 3 weeks. After 3 weeks, the plastic container setup was disassembled. The number of live termites in the experimental unit was recorded. The amount of mixture 550 displaced from embodiment 2 was measured and recorded. These data were compared and are summarized in Table 3.

TABLE 3

Summary of mortality and amount of soil moved when treated with 125.0 ppm chlorfenapyr.

| Treatment | Replications | Alive | % Mortality | Soil Moved (g) |
| --- | --- | --- | --- | --- |
| Untreated Control | 1 | 452 | 9.6 | 4.93 |
| Chlorfenapyr 125 | 1 | 0 | 100.0 | 0.81 |
| Chlorfenapyr 125 | 2 | 0 | 100.0 | 1.04 |
| Chlorfenapyr 125 | 3 | 0 | 100.0 | 1.33 |
| Chlorfenapyr 125 | 4 | 0 | 100.0 | 0.48 |

Alive refers to number of termites alive after three(3) weeks exposure. %Mortality refers to percentage of termites that died after three(3) weeks exposure. Soil Moved(g) refers to total amount soil removed by the termites per each replication(per experimental unit).

An average of 100.0% of the termites in treated units died, compared with approximately 9.6% mortality in the control unit. Additionally, significantly more of the untreated mixture 550 was moved into the termite galleries and living spaces when compared with the treated mixture 550. Total untreated mixture 550 moved from embodiment 3 to the surrounding area was approximately 4.93 g, compared with an average of approximately 0.92 g of mixture 550 treated with approximately 125.0 ppm chlorfenapyr.

In the second experiment, mixture 550 was tested at a concentration of approximately 12.5 ppm chlorfenapyr. Experimental procedure was identical to what is listed above. Results were compared and are summarized in Table 5.

TABLE 4

Summary of mortality and amount of soil moved when treated with approximately 12.5 ppm chlorfenapyr.

| Treatment | Replications | Alive | % Mortality | Soil Moved (g) |
| --- | --- | --- | --- | --- |
| Untreated Control | 1 | 407 | 18.6 | 2.02 |
| Untreated Control | 2 | 413 | 17.4 | 1.71 |
| Untreated Control | 3 | 400 | 20.0 | 2.93 |
| Untreated Control | 4 | 393 | 21.4 | 2.16 |
| Untreated Control | 5 | 425 | 15.0 | 2.72 |
| Chlorfenapyr 12.5 | 1 | 433 | 13.4 | 0.00 |
| Chlorfenapyr 12.5 | 2 | 405 | 19.0 | 0.01 |
| Chlorfenapyr 12.5 | 3 | 383 | 23.4 | 0.62 |
| Chlorfenapyr 12.5 | 4 | 336 | 32.8 | 1.06 |
| Chlorfenapyr 12.5 | 5 | 0 | 100.0 | 1.41 |

There was no significant difference in mortality with mixture 550 treated with approximately 12.5 ppm chlorfenapyr when compared with untreated controls. An average of approximately 37.7% of the termites in treated units died, compared with approximately 18.5% mortality in the untreated control units. However, there was significantly less treated mixture 550 moved into the termite galleries and living spaces when compared with the untreated mixture 550. Average untreated mixture 550 moved from embodiment 3 to the surrounding area was approximately 2.31 g, compared with an average of approximately 0.62 g of mixture 550 treated with approximately 12.5 ppm chlorfenapyr.

In summary, the lack movement by the termites of treated mixture 550 into their galleries and living spaces resulted in poor mortality when approximately 12.5 ppm chlorfenapyr was used in embodiment 3. The range of untreated mixture 550 moved was between approximately 1.71 and approximately 2.93 g. The one experimental unit with treated mixture 550 that resulted in 100% mortality, approximately 1.41 g of mixture 550 was moved into the termite galleries and living spaces. Thus, if the termites come into contact with the mixture 550 treated at approximately 12.5 ppm chlorfenapyr, they can move it and subsequently die.

Fourth Embodiment

FIG. 10 is an exploded view of a fourth embodiment 700 of the invention. FIG. 11A is a front/back view of a frame holder 705 for the fourth embodiment 700. FIG. 11B is a side view of the frame holder 705 of FIG. 11A along arrow D1. FIG. 11C is a bottom view of the frame holder 705 of FIG. 11A along arrow D2.

Embodiment 700 is a modification of the third embodiment and includes the housing 500 having the mixture 540 of the slow-acting toxin mixed with the non-edible foraging matrix, which in turn can be inserted into main housing chamber 605, which can in turn be inserted into frame 705. The frame 705 can be formed from a durable material such as but not limited to rust resistant metal, plastics, and the like, and combinations thereof. The rust resistant metal can include but not be limited to aluminum, galvanized metal, and the like, and combinations, thereof. The plastics can include but not be limited to hard or soft plastics, fiberglass, and the like, and combinations thereof. The frame 705 can be substantially rectangular and have front and back walls 710 each having dimensions that can be approximately 6 cm by approximately 7.4 cm, a bottom wall 73 having dimensions of approximately 3.2 cm by approximately 7.4 cm, and side walls 720 having dimensions of approximately 6 cm by approximately 3.2 cm. An opening in the top 740 can allow for the insertion of the housing 500 and main housing 605 as shown by arrows D4 and D5. Each of the walls 710, 720 and 730 can have side through-hole, slots 715, 725, 735 that allow arthropods such as termites to enter into and pass out of the frame 705. Embodiment four can also be inserted into the ground adjacent to any known arthropod paths(termite habitats) as similarly described in the previous embodiments. The non-decomposable frame 705 allows for users to substitute into the frame new housings 500 and main housings 605 over time as the latter decompose and/or become obsolete. The durable frames 705 allow for users to utilize identical ground insertion locations over time.

Fifth Embodiment

FIG. 12 is an exploded view of a fifth embodiment 800 of the invention. FIG. 13A is an assembled view of the fifth embodiment 800 of FIG. 12. FIG. 13B is a front view of the fifth embodiment 800 of FIG. 12. FIG. 13C is a side view of the embodiment 800 of FIG. 13B along arrow E1. FIG. 13D is a top view of the embodiment 800 of FIG. 13B along arrow E2. FIG. 13E is a bottom view of the embodiment 800 of FIG. 13B along arrow E3. The fifth embodiment is a further modification of the second embodiment described in reference to FIGS. 6–7C.

Referring to FIGS. 12 and 13A–13C, fifth embodiment 800 can have a rectangular outer shape with a staked bottom portion for allowing easy insertion into a ground surface. Embodiment 800 can have a first wall 810, stake shaped bottom 815 and second wall 830 with stake shaped bottom 835 that can be sandwiched together with side perimeter members 822, 824, 826, 828 all together forming a chamber space 840 therebetween. Walls 810, 330 and side perimeter members 822, 824, 826, 828 can each be formed from an edible non-toxic food source such as wood, paper, cellulose material, foam, plastic, combinations thereof, and the like, that can be fastened together by for example, with a non-toxic adhesive such glue, and the like. For example, preferred embodiment 800 can have walls 810, 830 with bottom stake portions 815, 835 formed from wood, and side perimeter members 822, 824, 826, 828 formed from foam, and glue joining these components together in a sandwich configured chamber 800. The upper portion 842 of inner space 840 can be open to allow the mixture 850(not shown) of the slow acting toxicant (previously described) and non-edible foraging matrix (previously described) to be inserted inside.

Approximate dimensions of the fifth embodiment 800 can includes a thickness of approximately 1.3 cm and a side lengths of each wall 810, 830 of approximately 5 cm, and a short width length of approximately 3.7 cm. The upper portion opening 842 can also include a cap member similar to the other members 822, 824, 826, 828 can be used to close off the interior mixture 829 of the slow acting toxicant mixed with the non-edible foraging matrix from being physically touched by the user. Still furthermore, a see-through material member such as clear plastic can be used to also cap the upper portion opening 842.

In application, the fifth embodiment 800 can be used in applications similar to those of the previous embodiments described. For example, embodiment 800 can be inserted into the ground adjacent to arthropods such as termites. The insertion can be done by placing the embodiment 800 into an existing hole in the ground. Still furthermore, the embodiment 800 can be manually pushed into the ground by contacting the stake portions 815, 835 first into the ground in selected locations about a structure that is to be protected. Similar to the previous embodiments, arthropods such as termites here would be attracted to the edible food source walls 810, 830, and/or side perimeter members 822, 824, 826, 828 and would then pass into the interior space 840 having the mixture 829 of the non-edible foraging matrix and slow acting toxicants that were previously described in the first embodiment, and then they would pass out of the chamber embodiment 800 to bring the slow acting toxicants back to their tunnels, colonies, nests, and the like, where the slow acting toxicants would kill the termites over time. Similar to the previous embodiments, the mixture 829 of slow acting toxicants and non-edible foraging matrix can be pre-packaged in a covering. Still furthermore, the mixture 829 can be poured into the opening 842 and into the chamber space 840 when it is about to be used. The stake portions 815, 835 can be narrow enough to allow for easy ground insertion, and can be very sharp or slightly rounded at their tip portions.

Sixth Embodiment

FIG. 14 is a perspective view of a sixth embodiment 900 of the invention that can be used with treating more than one arthropod at a time. For example, both termites and carpenter ants and fire ants can be simultaneously treated. FIG. 15A is a top view of the sixth embodiment 900 of FIG. 14. FIG. 15B is a side view or bottom view of the sixth embodiment 900 of FIG. 14. FIG. 15C is a cross-sectional view of the sixth embodiment 900 of FIG. 14 along arrow F.

Referring to FIGS. 14 and 15A–15C, embodiment 900 can be a rectangular shape such as a cube, and have top wall 910, side walls 920, 930 and bottom wall 940, can together form a frame for housing the novel interior layers 916 therein. The walls can be made from a long lasting material that does not easily deteriorate over time such as but not limited to rust resistant metal, aluminum, plastics, and the like, and combinations thereof. The top wall can have openings 915 such as but not limited to slots that are large enough to allow arthropods such as termites to enter inside, but also prevent the user from being able to physically contact the interior layers 916. Each of the walls can have dimensions of approximately 3 inches by approximately 3 inches, and completely enclose the novel interior layers 916.

In operation, arthropods enter housing 900 through openings 915 and can pass through airspace 917 to contact and pass through first layer 952 which can be an approximately ¼ inch layer comprised of the mixture of the foraging matrix and the slow-acting toxins that are previously described. Under first layer 952 is a second layer 954 such as an approximate ¼ inch layer of edible type material such as cellulose, followed by a third approximately ¼ inch layer 956 of the mixture of foraging non-edible matrix and slow-acting toxins, followed by a fourth approximately ¼ inch layer 958 of cellulose, followed by a fifth approximately ¼ inch layer 960 of mixture of foraging non-edible matrix and slow acting toxins, followed by a sixth approximately ¼ inch layer 962 of styrofoam, followed by a seventh approximately ¼ inch layer 964 of mixture of foraging non-edible matrix and slow acting toxins, followed by an eighth approximately ¼ inch layer 966 of cellulose, followed by a ninth approximately ¼ inch layer 968 of mixture of foraging non-edible matrix and slow acting toxins, followed by a tenth approximately ¼ inch layer 970 of styrofoam. The alternating layers of cellulose and styrofoam can be used to attract different arthropods through the mixtures of foraging matrix and slow-acting toxins to cause various arthropods such as termites and fire ants and carpenter ants to pass therethrough. The different arthropods can then take the slow-acting toxins back to their colonies, tunnels, and homes to be later destroyed, as previously described. The non-toxic layers can also function as attractants for the arthropods.

The outer walls 910–940 of the embodiment rectangular housing 900 can be formed from a laminated material such as but not limited to laminated plastics, and the like.

Embodiment 900 can be used by it or in combination with any attributes of the embodiments previously described. For example, the novel layers 916 can be substituted into any of the previous embodiments without the top wall 910 and side and bottom walls 920–940.

The attributes of each of the above embodiments can be used with one another. The term foam can include open celled foam, closed cell foam, Styrofoam, and the like, and combinations, thereof.

While some of the preferred embodiments have been described as being sandwich shaped, other shapes for the chambers can be used such as but not limited to disc shaped, cylindrical shaped, triangular shaped, and other various shapes, and the like.

Although some non edible foraging matrix materials were previously described other types of non edible foraging matrix materials can be used such as but not limited to soil, sand, gravel, rocks, pebbles, shale, expanded shale, clay, and any material that can be ground or fashioned to the particle size that termites and other arthropods can pick up with their mandible and forage through, or any other material that termites and other arthropods can tunnel through such as dental cast-stone and other such porous materials.

While the invention has been described using some types of slow-acting toxicants, other slow-acting toxicants can also be used such as but not limited to those listed in Table 5.

TABLE 5

Additional Slow-Acting Toxicants

| TYPE | Slow-Acting Toxicants |
| --- | --- |
| Non-repellents: | Chlorfenapyr, Imidacloprid, Fipronil |
| Bait materials: | Hydramethylnon, Sulfluramid, Hexaflumuron |
| IGRs: | Pyriproxyfen, methoprene and lufenuron, dimilin, |
| Others: | Chlorpyrifos, and their active derivatives. |
| Botanicals: | Neem (azadiractin), |
| Inorganics: | boric acid based |

Although some of the preferred embodiments have been described as for being used with termites, the embodiments can be used with other types of arthropods such as but not limited to carpenter ants, fire ants and roaches, and the like.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A composition for treating different arthropods, comprising:

alternating layers of a first layer directly against a second layer which is directly against a third layer, the first layer and the third layer each being a mixture layer of a non-edible foraging matrix mixed with a slow-acting and non-repellant toxicant, the foraging non-edible matrix includes at least one of: soil, sand, gravel, rocks, pebbles, shale, and mixtures thereof, and the second layer being a non-toxic layer, the non-toxic layer being an edible non-toxic attractant material; and a fourth layer being a nontoxic layer, the fourth layer directly against one of the first layer and the third layer, the fourth layer being a different nontoxic material than the second layer, the second layer and the fourth layer being used to attract different arthropods to the composition, wherein different arthropods can be treated over time.

2. The composition of claim 1, wherein the non-toxic layer includes: cellulose.

3. The composition of claim 1, wherein the non-toxic layer includes: foam.

4. The composition of claim 1, further comprising:

an outer covering to contain the alternating layers, the outer casing for allowing the alternating layers to be placed under ground, wherein the outer covering will allow arthropods to access the alternating layers.

5. The composition of claim 1, further comprising:

a non-toxic layer of air that the arthropods initially pass through to reach the first layer.

6. An apparatus for killing arthropods and protecting structures, comprising:

a first layer consisting of a mixture of a foraging non-edible foraging matrix mixed with a slow acting and non-repellant toxicant, the foraging non-edible matrix includes at least one of: soil, sand, gravel, rocks, pebbles, shale, and mixtures thereof;

a second layer of a non-toxic material that is an attractant to arthropods, the second layer being directly against one side of the first layer;

a third layer consisting of a mixture of a foraging non-edible foraging matrix mixed with a slow acting and non-repellant toxicant, the first layer being separated from the third layer by the second layer, the first layer having an identical composition to the third layer; and an alternating fourth layer of another non-toxic material that is an attractant to different arthropods from the second layer, the alternating layer being directly against another side of one of the first layer and the third layer, wherein arthropods pass into the apparatus and the slow acting and non-repellant toxicants destroys the arthropods in their colonies over time and protects structures.

7. The apparatus of claim 6, further comprising:

an alternating fifth layer of a foraging non-edible foraging matrix mixed with a slow acting and non-repellant toxicant which is directly against the fourth layer.

8. The apparatus of claim 7, wherein the different arthropods are selected from: termites, carpenter ants, fire ants, and roaches.

9. The apparatus of claim 6, further comprising:

a chamber for housing the first layer, the second layer, and the third layer having an entrance for the arthropods.

10. The apparatus of claim 6, wherein the first layer and the third layer are each approximately ¼ inch thick.

11. The apparatus of claim 6, wherein the second non-toxic layer is approximately ¼ inch thick.

12. The apparatus of claim 7, further comprising:

an alternating sixth layer of still another non-toxic material that is an attractant to different arthropods from the second layer and the fourth layer, the sixth layer directly against another side of the fifth layer; and an alternating seventh layer of a foraging non-edible foraging matrix mixed with a slow acting and non-repellant toxicant which is directly against the sixth layer.

* * * * *